United States Patent [19]

Dubief et al.

[11] Patent Number: 5,702,690

[45] Date of Patent: Dec. 30, 1997

[54] COMPOSITION FOR WASHING AND ANTIDANDRUFF TREATMENT OF HAIR AND THE SCALP, BASED ON SELENIUM SULPHIDE AND NONIONIC SURFACTANT OF THE POLYGLYCEROLATED OR ALKYLPOLYGLYCOSIDE TYPE

[75] Inventors: Claude Dubief, Le Chesnay; Danièle Cauwet, Paris, both of France

[73] Assignee: L'Oreal, Paris, France

[21] Appl. No.: 414,139

[22] Filed: Mar. 30, 1995

Related U.S. Application Data

[63] Continuation of Ser. No. 917,392, Jul. 23, 1992, abandoned.

[30] Foreign Application Priority Data

Jul. 25, 1991 [FR] France .................... 91 09450

[51] Int. Cl.⁶ .................... A61K 7/06; A61K 7/075
[52] U.S. Cl. .................... 424/70.1; 424/70.4; 424/70.5; 424/70.31; 424/DIG. 4; 514/880; 514/881
[58] Field of Search .................... 424/70, 70.1, 70.4, 424/70.5, 70.31, DIG. 4; 514/880, 881

[56] References Cited

U.S. PATENT DOCUMENTS

| | | | |
|---|---|---|---|
| 4,454,316 | 6/1984 | Veeder et al. | 536/123 |
| 4,927,563 | 5/1990 | McCall | 424/70 |
| 5,196,029 | 3/1993 | Kawase | 424/70 |

FOREIGN PATENT DOCUMENTS

| | | |
|---|---|---|
| 0023397 | 2/1981 | European Pat. Off. . |
| 0064354 | 11/1982 | European Pat. Off. . |
| 0079038 | 5/1983 | European Pat. Off. . |
| 0127698 | 12/1984 | European Pat. Off. . |
| 0317314 | 5/1989 | European Pat. Off. . |
| 0422508 | 4/1991 | European Pat. Off. . |
| 2058106 | 4/1981 | United Kingdom . |
| 2058107 | 4/1981 | United Kingdom . |
| 2164658 | 3/1986 | United Kingdom . |

*Primary Examiner*—Gollamudi S. Kishore
*Attorney, Agent, or Firm*—Jacobson, Price, Holman & Stern, PLLC

[57] ABSTRACT

The present invention relates to a composition for washing and antidandruff treatment of hair and the scalp, containing in an aqueous medium at least selenium sulphide, at least one nonionic surface-active agent of the polyglycerolated or alkylpolyglycoside type, and at least one suspending agent chosen from the anionic cellulose derivatives and the biopolysaccharides.

11 Claims, No Drawings

COMPOSITION FOR WASHING AND ANTIDANDRUFF TREATMENT OF HAIR AND THE SCALP, BASED ON SELENIUM SULPHIDE AND NONIONIC SURFACTANT OF THE POLYGLYCEROLATED OR ALKYLPOLYGLYCOSIDE TYPE

This application is a continuation of Ser. No. 07/917,392, filed Jul. 23, 1992, now abandoned.

The present invention relates to cosmetics compositions for washing and antidandruff treatment of hair and the scalp, based on selenium sulphide and nonionic surface-active agent of the polyglycerolated or alkylpolyglycoside type.

Selenium sulphide is well known in the cosmetics field for its antidandruff properties. Shampoo compositions of the state of the art which contain this active compound generally contain anionic or nonionic surfactants.

Selenium sulphide exists in the suspended powder form in these compositions. The resulting suspensions, however, have an inadequate stability on storage which is shown by a strong coloration during the period of storage.

The Applicant has discovered, surprisingly, that by combining nonionic surface-active agents of the polyglycerolated or alkylpolyglycoside type and certain suspending agents with the selenium sulphide, the stability of the resulting suspension was substantially increased.

The compositions of the invention indeed have a better colour and homogeneity stability over time.

They additionally have a better skin tolerance and a better foaming ability than those of the compositions based on nonionic surfactants of the prior art.

The subject of the invention is thus a composition for washing and antidandruff treatment of the hair and the scalp, based on selenium sulphide and nonionic surfactant of the polyglycerolated or alkylpolyglycoside type and a particular suspending agent such as defined below.

Another subject of the invention consists in a process for washing and cosmetic treatment in order to remove dandruff from hair, using these compositions.

Other subjects will become apparent in the light of the description and the examples which follow.

The compositions in accordance with the present invention are essentially characterised in that they contain in an aqueous medium:

a) at least selenium sulphide in suspension;

b) at least one nonionic surfactant of the polyglycerolated type or the alkylpolyglycoside type;

c) at least one suspending agent chosen from the anionic cellulose derivatives and the biopolysaccharides.

The selenium sulphide used in accordance with the present invention contains one selenium atom for two sulphur atoms. It can have a cyclic structure $Se_xS_y$ in which $x+y=8$.

The selenium disulphide which can be used according to the invention is a powder whose particles have a particle size of less than 200 microns and preferably less than 25 microns.

The selenium sulphide is present in the compositions in accordance with the invention in proportions preferably of between 0.1 and 5% and more particularly between 0.6 and 2.5% by weight in relation to the total weight of the composition.

The nonionic surface-active agents of the polyglycerolated type in accordance with the present invention are chosen from the following polyhydroxypropyl ether compounds:

(A) The compounds corresponding to the formula (I):

in which $R_1$ denotes an alkyl radical or a mixture of alkyl radicals containing 10 to 14 carbon atoms and m is an integer or decimal number from 2 to 10, and preferably from 3 to 6. These compounds of formula (I) can be prepared according to the process described in Patent FR-A-1,477,048;

(B) The compounds corresponding to the formula (II):

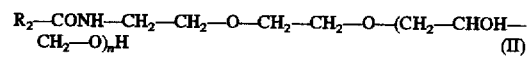

in which $R_2$ denotes an alkyl and/or alkenyl radical or a mixture of alkyl and/or alkenyl radicals having from 11 to 17 carbon atoms and n denotes an integer or decimal number from 1 to 5, and preferably from 1.5 to 4. These compounds of formula (II) can be prepared according to the process described in the Patent FR-A-2,328,763;

(C) The compounds corresponding to the formula (III):

in which R3 denotes an aliphatic, cycloaliphatic or arylaliphatic radical, preferably having from 7 to 21 carbon atoms, and their mixtures, the aliphatic chains in particular denoting alkyl chains which are able to contain 1 to 6 ether, thioether and/or hydroxymethylene groups and p is between 1 and 10 inclusive.

These compounds are prepared by condensation, using alkaline catalysis, of 2 to 10, and preferably of 2.5 to 6, moles of glycidol with an alpha diol or a mixture of $C_{10}$-$C_{14}$ alpha diols at a temperature of 120°–180° C. and preferably from 140° to 160° C., the glycidol being slowly added according to the preparation process described in Patent FR-A-2,091,516;

(D) The compounds prepared by condensation, using acid catalysis, of 2 to 10, and preferably of 2.5 to 6, moles of glycidol per mole of alcohol or alpha diol containing 10 to 14 carbon atoms, at a temperature of 50° to 120° C., the glycidol being slowly added to the alcohol or to the alpha diol. The preparation process of these compounds is described more particularly in Patent FR-A-2,169,787;

(E) The polyhydroxypropyl ether compounds prepared by polyaddition of glycerol monochlorohydrin to a polyhydroxylated organic compound in the presence of a strong base with removal, by distillation, of the water as it is formed. These compounds are described in particular in French Patent FR-A-2,574,786.

Among the nonionic surfactants of the polyhydroxypropyl ether family described in paragraphs (A), (B), (C), (D) and (E) above, the preferred compounds are represented by the formulae:

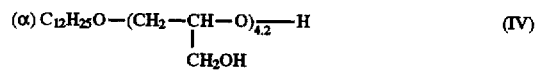

where $R_1$ denotes a mixture of $C_{10}H_{21}$ and $C_{12}H_{25}$ alkyl radicals;

(β) the compounds prepared by condensation, using alkaline catalysis, of 3.5 moles of glycidol with an alpha diol having 12 carbon atoms, according to the process described in Patent FR-A-2,091,516;

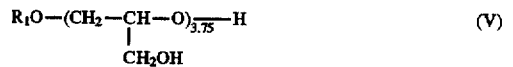

(γ) the compounds corresponding to the formula:

$$R_2\text{—CONH—CH}_2\text{—CH}_2\text{—O—CH}_2\text{—CH}_2\text{—O—(CH}_2\text{—CHOH—CH}_2\text{—O)}_{3.5}H \quad \text{(VI)}$$

where $R_2$ denotes a mixture of radicals comprising the following alkyl and alkenyl radicals:

$C_{11}H_{23}$, $C_{13}H_{27}$, the radicals derived from copra fatty acids and the radical derived from oleic acid;

(δ) the compounds prepared by condensation of 3.5 moles of glycidol with a mixture of $C_{11}$–$C_{14}$ alpha diols, described in the Patent FR-A-2,091,516.

The polyhydroxypropyl ether nonionic surfactant obtained by condensation of glycerol monochlorohydrin (2.5 moles) with 1,2-dodecanediol in the presence of sodium hydroxide is more particularly preferred.

The alkylpolyglycosides used in accordance with the invention correspond in particular to the following formula (VII):

$$RO(C_6H_{10}O_5)_x\text{—H} \quad \text{(VII)}$$

or also corresponding to the expanded structure (VIII):

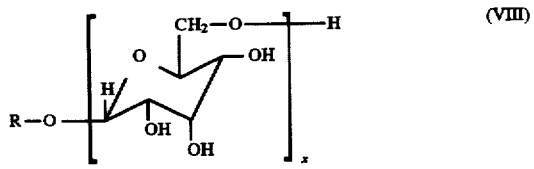

in which:

R denotes a $C_8$–$C_{24}$, straight- or branched-chain alkyl or alkenyl radical or a mixture of $C_8$–$C_{24}$, straight- or branched-chain alkyl or alkenyl radicals; x is a number from 1 to 15.

The alkylpolyglycoside compounds of expanded formula (VIII) defined above, used in accordance with the invention, are preferably represented by the products sold by the Company Henkel under the name APG, such as the products APG 300, APG 350, APG 500, APG 550, APG 625, APG base 10–12; the compounds sold by the Company Seppic under the names Triton CG 110 (or Oramix CG 110) and Triton CG 312 (or Oramix NS 10); those sold by the Company BASF under the name Lutensol GD 70.

The compositions according to the invention contain the nonionic surfactant(s) in proportions of preferably between 5 and 50% by weight in relation to the total weight of the composition and more particularly between 8 and 30% by weight.

The suspending agents, which can be used according to the invention, are chosen from the anionic cellulose derivatives, such as sodium carboxymethyl cellulose and the biopolysaccharides such as the xanthan or scleroglucan gums, optionally combined with inorganic silicon derivatives chosen from the oxide and the silicates, especially the double silicates of magnesium and aluminium.

The biopolysaccharides used are products containing, in their structure, glucose, mannose, glucuronic or galacturonic acid or D-glucopyranose or galactose units.

Among these compounds, there may be mentioned the xanthan gum obtained by the action of the bacterium *Xanthomonas campestri* and the mutants or variants, which has a molecular weight of between 1,000,000 and 50,000,000. Xanthangums have a viscosity of between 0.60 and 1.65 Pa s as an aqueous composition containing 1% of xanthan gum, measured in a Brookfield LVT type viscometer at 60 revolutions/minute. These gums, which are heterobiopolysaccharides, contain 3 different monosaccharides in their structure, which are mannose, glucose and glucuronic acid. The particularly preferred products are those marketed under the name "Keltrol" by the Comapny Kelco, Kelzan S marketed by the company Kelco, Rhodopol 23 SC marketed by the Company Rhone-Poulenc, Rhodigel 23 sold by the Company Rhone-Poulenc, Deuteron XG marketed by the Company Schoener GmbH, Actigum CX9 marketed by the company Ceca/Satia, the products sold by the Company Kelco under the names "Kelzan K3 B130, K8 B12".

Other biopolysaccharides which can be used in accordance with the invention can be chosen from the biopolymer PS 87 generated by the bacterium *Bacillus polymyxa* which contains glucose, galactose, mannose, fucose and glucuronic acid in its structure; this biopolymer PS 87 is described in the European Patent Application published as No. 023397; the biopolymer S88 generated by the strain *Pseudomonas* ATCC 31554, which contains rhamnose, glucose, mannose and glucuronic acid in its structure; this biopolymer is described in British Patent No. 2,058,106; the biopolymer S130 is generated by the strain *Alcaligenes* ATCC 31555, which contains rhamnose, glucose, mannose and glucuronic acid in its molecule; this biopolymer is described in British Patent No. 2,058,107; the biopolymer S139 generated by the strain *Pseudomonas* ATCC 31644, which contains rhamnose, glucose, mannose, galactose and galacturonic acid in its molecule; this biopolymer is described in particular in U.S. Pat. No. 4,454,316; the biopolymer S 198 generated by the strain *Alcaligenes* ATCC 31853, which contains rhamnose, glucose, mannose and glucuronic acid in its molecule; this biopolymer is described in European Patent Application 64,354.

The biopolymer BM07 described in European Application EP 351,303, containing units derived from glucose, galactose and pyruvic, succinic and acetic acids in its molecule.

The biopolymer AM-2, which contains glucose, rhamnose, mannose and glucuronic acid in its molecule, described in European Application 127,698, or those described in European Application 79038 containing glucose, galactose, mannose and glucuronic acid in their molecule.

The *scleroglucans* used in accordance with the invention are neutral polysaccharides of microbial origin, obtained by aerobic fermentation of a glucose-containing medium with a fungus of the Sclerotium type and have the structure of a homopolymer of D-glucopyranose.

The scleroglucans correspond to the formula:

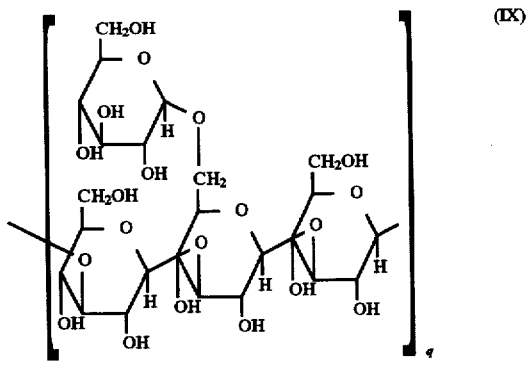

where q (degree of polymerisation) varies from 500 to 1600.

The scleroglucans used in accordance with the invention are represented by the products sold under the name Actigum CS by the Company Sanofi Bio Industries, and in particular Actigum CS 11, and under the name Amigel by the Company Alban Muller International. Other scleroglucans, such as that treated with glyoxal and described in Patent Application FR 2,633,940, can also be used.

The suspending agents such as defined above are present in the compositions of the invention in proportions of preferably between 0.2 and 5% by weight in relation to the total weight of the composition and more particularly between 0.5 and 3% by weight.

The compositions according to the invention can contain, as well as the suspending agents defined previously, other suspending agents chosen from:

A/The compounds of the following formula:

$$R'X \qquad (X)$$

in which R' is an aliphatic radical with a long carbon chain, optionally interrupted by oxygen atoms, and X is a carboxylic, sulphuric or phosphoric acid residue or a radical derived from a carboxylic acid or an amide.

The preferential compounds of formula (X) are chosen from those in which:

(i) R' is a $C_{11}$–$C_{21}$ alkyl or alkenyl radical, and X is:

a group COOA where A is a mono- or polyhydroxyalkyl radical derived from a $C_2$–$C_3$ polyol or a radical $CH_2CH_2SO_3M$ where M denotes an alkali metal, ammonium or a $C_1$–$C_4$ alkanolamine residue;

a group $CO(OCH_2CH_2)_r$—OH where r has a value of between 2 and 150;

a group

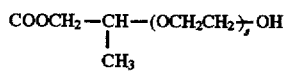

where s has a value of between 2 and 150; the free OH functional groups of the groups defined above being optionally esterified with an acid R"COOH where R" is a $C_{11}$–$C_{21}$ alkyl or alkenyl;

a group $CONR_4R_5$ where $R_4$ and $R_5$ represent hydrogen or $C_1$–$C_4$ hydroxyalkyl, one at least representing a $C_1$–$C_4$ hydroxyalkyl;

a group $OSO_3M$ or $1/3\ PO_4^{3-}M_3$ where M represents an alkali metal, ammonium or a $C_1$–$C_4$ alkanolamine residue;

(ii) R' denotes a radical $R_6(OC_2H_4)_l$—$OCH_2$ and X denotes a group COOM where M has the meaning shown above, $R_6$ denoting a $C_{12}$–$C_{14}$ alkyl radical and l an integer or a decimal number of between 2.5 and 10; or else $R_6$ denotes oleyl and l varies from 2 to 9 or else $R_6$ denotes ($C_8$–$C_9$)-alkylphenyl and l varies from 4 to 8;

(iii) R' denotes a ($C_{12}$–$C_{16}$)alkyl ether group and X a group $CONR_4R_5$, in which $R_4$ and $R_5$ have the same meaning as that shown above.

B/The oxides of dimethyl($C_{16}$–$C_{22}$)alkylamines;

C/Another suspending agent which can be used according to the invention is an alcohol having 27 to 44 carbon atoms and containing one or two ether and/or thioether or sulphoxide groups, corresponding to the formula:

$$R_7\text{—}Z\text{—}[C_2H_3(OH)]\text{—}CH_2\text{—}Y\text{—}R_8 \qquad (XI)$$

in which:

$R_7$ and $R_8$, which are identical or different, denote $C_{12}$–$C_{20}$ linear alkyl groups;

Z denotes an oxygen atom, a sulphur atom or a sulphoxide group;

Y denotes an oxygen atom, a sulphur atom, a sulphoxide group or a methylene group;

the sum of the carbon atoms of $R_7$ and $R_8$ varies from 24 to 40;

in the case where Y denotes a methylene group, the sum of the carbon atoms preferably varies from 26 to 36 inclusive, and when Y does not denote a methylene group, the sum of the carbon atoms of $R_7$ and $R_8$ preferably varies from 28 to 36 inclusive; when Z or Y denotes sulphoxide, Y or Z does not denote sulphur.

The pH of the compositions in accordance with the present invention is generally between 2 and 9 and more particularly between 3 and 6.

The aqueous medium of the compositions according to the invention can consist solely of water or of a mixture of water and a cosmetically acceptable solvent, such as $C_1$–$C_4$ lower alcohols, such as ethanol, isopropanol or n-butanol, or alkylene glycols such as ethylene glycol or the glycol ethers.

According to a preferred embodiment of the invention, the composition contains an alkylpolyglycoside, selenium sulphide, a biopolysaccharide and an inorganic derivative of silicon chosen from the oxide or the silicates, in the concentrations defined above.

The cosmetic compositions according to the invention can be in the form of more or less thick liquids, of gels, of creams or of aerosol foams.

The compositions in accordance with the invention can optionally additionally contain various additives which do not alter the stability of the compositions, such as anionic, amphoteric or zwitterionic surface-active agents, nonionic surface-active agents other than those described previously, anionic, nonionic, cationic or amphoteric polymers, proteins, oils, waxes, silicone resins and/or gums, acidifying or alkalifying agents, preserving agents, fragrances or other adjuvants commonly used in cosmetics.

They can also contain antibacterial agents such as chloramine T, chloramine B, 1,3-dibromo-5,5-dimethyl-hydantoin, 1,3-dichloro-5,5-dimethylhydantoin, 3-bromo-1-chloro-5,5-dimethylhydantoin or N-chlorosuccinimide.

The compositions according to the invention are preferably used as shampoos for washing and treating hair and the scalp and they are applied, in that case, to wet or dry hair in quantities which are effective for washing them, this application being followed by a rinsing.

The examples which follow illustrate the present invention without, however, having a limiting character.

EXAMPLE 1

A shampoo of the following composition is prepared:

| | | |
|---|---|---|
| ($C_9$-$C_{10}$-$C_{11}$/20-40-40)Alkylpolyglycoside sold at a concentration of 50% AS by the Company Henkel under the name APG 300 | | 15.0 g AS |
| Micronised selenium sulphide, sold by the Company Urquima (mean diameter 7.2 microns) | | 1.0 g |
| Xanthan gum sold under the name Keltrol T by the Company Kelco | | 1.0 g |
| Hydrochloric acid | qs pH = | 4.5 |
| Preserving agent | qs | |
| Water | qs | 100 g |

EXAMPLE 2

A shampoo of the following composition is prepared:

| | | |
|---|---|---|
| Polyhydroxypropyl ether nonionic surfactant prepared by condensation, using alkaline catalysis, of 3.5 moles of glycidol with a mixture of alpha diols having 10 to 14 carbon atoms, according to the process decribed in Patent FR No. 71-17206 (2,091,516) | | 15.0 g |
| Micronised selenium sulphide, sold by the Company Urquima (mean diameter 7.2 microns) | | 1.0 g |
| Xanthan gum sold under the name Keltrol T by the Company Kelco | | 1.0 g |
| Hydrochloric acid | qs pH = | 4.5 |

-continued

| | | |
|---|---|---|
| Preserving agent | qs | |
| Water | qs | 100 g |

EXAMPLE 3

A shampoo of the following composition is prepared:

| | | |
|---|---|---|
| Polyhydroxypropyl ether nonionic surfactant prepared by condensation, using alkaline catalysis, of 3.5 moles of glycidol with a mixture of alpha diols having 10 to 14 carbon atoms, according to the process decribed in Patent FR No. 71-17206 (2,091,516) | | 15.0 g |
| Micronised selenium sulphide, sold by the Company Urquima (mean diameter 7.2 microns) | | 1.0 g |
| Xanthan gum sold under the name Keltrol T by the Company Kelco | | 0.8 g |
| Monoisopropanolamide of coconut acid | | 2.0 g |
| Compound of formula (XI) in which: $R_7 = C_{16}H_{33}$, $R_8 = C_{14}H_{29}$ $Z = O$, $Y = CH_2$ prepared by reaction of 3 moles of alcohol with one mole of epoxide, used without purification | | 2.0 g |
| Buffered solution (citric acid, hydrochloric acid, sodium hydroxide) | qs pH = | 4 |
| Preserving agent | qs | |
| Water | qs | 100 g |

EXAMPLE 4

A shampoo of the following composition is prepared:

| | | |
|---|---|---|
| ($C_9$-$C_{10}$-$C_{11}$/20-40-40)Alkylpolyglycoside sold at a concentration of 50% AS by the Company Henkel under the name APG 300 | | 8.0 g AS |
| Micronised selenium sulphide, sold by the Company Urquima (mean diameter 7.2 microns) | | 0.6 g |
| Xanthan gum sold under the name Keltrol T by the Company Kelco | | 0.8 g |
| Diethanolamide of coconut acid | | 1.0 g |
| Ethylene glycol distearate | | 2.0 g |
| Buffered solution (citric acid, hydrochloric acid, sodium hydroxide) | qs pH = | 4 |
| Preserving agent | qs | |
| Water | qs | 100 g |

EXAMPLE 5

A shampoo of the following composition is prepared:

| | | |
|---|---|---|
| Polyhydroxypropyl ether nonionic surfactant prepared by condensation, using alkaline catalysis, of 3.5 moles of glycidol with a mixture of alpha diols having 10 to 14 carbon atoms, according to the process decribed in Patent FR No. 71-17206 (2,091,516) | | 8.0 g |
| Micronised selenium sulphide, sold by the Company Urquima (mean diameter 7.2 microns) | | 0.6 g |
| Xanthan gum sold under the name Keltrol T by the Company Kelco | | 0.8 g |
| Diethanolamide of coconut acid | | 1.0 g |
| Ethylene glycol distearate | | 2.0 g |
| Buffered solution (citric acid, hydrochloric acid, sodium hydroxide) | qs pH = | 4 |
| Preserving agent | qs | |
| Water | qs | 100 g |

EXAMPLE 6

A shampoo of the following composition is prepared:

| | | |
|---|---|---|
| Polyhydroxypropyl ether nonionic surfactant prepared by condensation, using alkaline catalysis, of 3.5 moles of glycidol with a mixture of alpha diols having 10 to 14 carbon atoms, according to the process decribed in Patent FR No. 71-17206 (2,091,516) | | 15.0 g |
| Micronised selenium sulphide, sold by the Company Urquima (mean diameter 7.2 microns) | | 1.0 g |
| Xanthan gum sold under the name Keltrol T by the Company Kelco | | 0.8 g |
| Monoisopropanolamide of coconut acid | | 2.0 g |
| Ethylene glycol distearate | | 2.0 g |
| Buffered solution (citric acid, hydrochloric acid, sodium hydroxide) | qs pH = | 4 |
| Preserving agent | qs | |
| Water | qs | 100 g |

EXAMPLE 7

A shampoo of the following composition is prepared:

| | | |
|---|---|---|
| ($C_9$-$C_{10}$-$C_{11}$/20-40-40)Alkylpolyglycoside sold at a concentration of 50% AS by the Company Henkel under the name APG 300 | | 5.0 g AS |
| Micronised selenium sulphide, sold by the Company Urquima (mean diameter 7.2 microns) | | 0.75 g |
| Sodium carboxymethyl cellulose sold under the name Blanose 7 M8/SF by the Company Aqualon | | 4.0 g |
| Buffered solution (citric acid, hydrochloric acid, sodium hydroxide) | qs pH = | 4 |
| Preserving agent | qs | |
| Water | qs | 100 g |

EXAMPLE 8

A shampoo of the following composition is prepared:

| | | |
|---|---|---|
| ($C_9$-$C_{10}$-$C_{11}$/20-40-40)Alkylpolyglycoside sold at a concentration of 50% AS by the Company Henkel under the name APG 300 | | 10.0 g AS |
| Selenium sulphide sold by the Company Sigma (particle size: 10% < 4 µm, 55% > 15 µm, 10% < 200 µm) | | 2.0 g |
| Xanthan gum sold under the name Keltrol T by the Company Kelco | | 1.5 g |
| Copolymer of vinylpyrrolidone and of dimethyl-aminoethyl methacrylate quaternised with diethyl sulphate, sold at a concentration of 20% AS under the name Gafquat 755 by the Company GAF | | 0.3 g AS |
| Sodium hydroxide | qs pH = | 7 |
| Preserving agent | qs | |
| Water | qs | 100 g |

EXAMPLE 9

A shampoo of the following composition is prepared:

| | | |
|---|---|---|
| Polyhydroxypropyl ether nonionic surfactant prepared by condensation, using alkaline catalysis, of 3.5 moles of glycidol with a mixture of alpha diols having 10 to 14 carbon atoms, according to the process decribed in Patent FR No. 71-17206 (2,091,516) | | 10.0 g |
| Selenium sulphide sold by the Company Sigma (particle size: 10% < 4 µm, 55% > 15 µm, 10% < 200 µm) | | 1.0 g |

-continued

| | | |
|---|---|---|
| Xanthan gum sold under the name Keltrol T by the Company Kelco | | 1.5 g |
| Spontaneous pH = | | 4 |
| Preserving agent | qs | |
| Water | qs | 100 g |

EXAMPLE 10

A shampoo of the following composition is prepared:

| | | |
|---|---|---|
| ($C_9$-$C_{10}$-$C_{11}$/20-40-40)Alkylpolyglycoside sold at a concentration of 50% AS by the Company Henkel under the name APG 300 | | 15 g AS |
| Micronised selenium sulphide, sold by the Company Urquima (mean diameter 7.2 microns) | | 1 g |
| Double silicate of magnesium and aluminium ($SiO_2$:66.5%/$Al_2O_3$:16.4%/MgO:3.38%) sold under the name Gel White HNF by the Company ECCI | | 2 g |
| Xanthan gum sold under the name Keltrol T by the Company Kelco | | 0.7 g |
| Mixture of two silicones (polydimethylsiloxane) of different viscosities sold under the name CF 1241 by the Company General Electric | | 3 g |
| Chloramine-T | | 0.088 g |
| Buffered solution (citric acid, hydrochloric acid, sodium hydroxide) | qs pH = | 4 |
| Water | qs | 100 g |

EXAMPLE 11

A shampoo of the following composition is prepared:

| | | |
|---|---|---|
| ($C_9$-$C_{10}$-$C_{11}$/20-40-40)Alkylpolyglycoside sold at a concentration of 50% AS by the Company Henkel under the name APG 300 | | 15 g AS |
| Micronised selenium sulphide, sold by the Company Urquima (mean diameter 7.2 microns) | | 1 g |
| Double silicate of magnesium and aluminium ($SiO_2$:66.5%/$Al_2O_3$:16.4%/MgO:3.38%) sold under the name Gel White HNF by the Company ECCI | | 2 g |
| Xanthan gum sold under the name Keltrol T by the Company Kelco | | 0.7 g |
| Buffered solution (citric acid, hydrochloric acid, sodium hydroxide) | qs pH = | 4 |
| Preserving agent | qs | |
| Water | qs | 100 g |

EXAMPLE 12

A shampoo is prepared by replacing the double silicate of magnesium and aluminium (Gel White HNF) in the composition of Example 11 with the silica sold under the name Aerosil 300 ($SiO_2$>98.8 %) by the Company Degussa.

EXAMPLE 13

A shampoo of the following composition is prepared:

| | | |
|---|---|---|
| ($C_9$-$C_{10}$-$C_{11}$/20-40-40)Alkylpolyglycoside sold at a concentration of 50% AS by the Company Henkel under the name APG 300 | | 20 g AS |
| Micronised selenium sulphide, sold by the Company Urquima (mean diameter 7.2 microns) | | 1 g |
| Silica sold under the name Aerosil 300 ($SiO_2$ > 98.8%) by the Company Degussa | | 2 g |
| Sodium carboxymethyl cellulose sold under the name Blanose 7 M8/SF by the Company Aqualon | | 3 g |
| Mixture of two silicones (polydimethylsiloxane) of different viscosities, sold under the name CF 1241 by the Company General Electric | | 3 g |
| Chloramine-T | | 0.088 g |
| Buffered solution (citric acid, hydrochloric acid, sodium hydroxide) | qs pH = | 4 |
| Water | qs | 100 g |

We claim:

1. Cosmetic composition for washing and antidandruff treatment of hair and the scalp containing in an aqueous medium at least:

a) from 0.1 to 5% by weight of selenium sulphide in suspension;

b) from 5 to 50% by weight of a polyglycerolated or alkylpolyglycoside nonionic surfactant selected from the group consisting of:

(A) compounds prepared by condensation, using acid catalysis, of 2 to 10 moles of glycidol per mole of alcohol or alpha diol containing 10 to 14 carbon atoms, at a temperature of 50° to 120° C.; and (B) compound corresponding to the following formula:

$$RO(C_6H_{10}O_5)_x\text{—H} \qquad \text{(VII)}$$

which has the expanded structure (VIII):

$$\left[ R-O-\begin{array}{c} CH_2-O-\\ O\\ H\\ OH\\ OH \end{array}-H \right]_x \qquad \text{(VIII)}$$

in which R denotes a $C_8$–$C_{24}$ straight- or branched-chain alkyl or alkenyl radical or a mixture of $C_8$–$C_{24}$ straight- or branched-chain alkyl or alkenyl radicals and x is a number from 1 to 15; and c) from 0.2 to 5% by weight of a suspending agent consisting essentially of xanthan gum or scleroglucan gum;

the percentages by weight being determined relative to the total weight of the composition.

2. Composition according to claim 1, where the selenium sulphide is in the form of a powder whose particles have a particle size of less than 200 microns.

3. Composition according to claim 1, where the polyglycerolated nonionic surfactant is selected from the group consisting of:

(α) the compounds prepared by condensation, using alkaline catalysis, of 3.5 moles of glycidol with an alpha diol having 12 carbon atoms; and (β) the compounds prepared by condensation of 3.5 moles of glycidol with a mixture of $C_{11}$–$C_{14}$ alpha diols.

4. Composition according to claim 1, where the biopolysaccharide is selected from the group consisting of:

the xanthan gums obtained by the action of the bacterium *Xanthomonas campestri* and its mutants or variants, comprising mannose, glucose and glucuronic acid in their structure, which have a molecular weight of between 1,000,000 and 50,000,000;

the biopolymer PS 87 generated by the bacterium *Bacillus polymyxa*, containing glucose, galactose, mannose, fucose and glucuronic acid in its structure;

the biopolymer S88 generated by the strain *Pseudomonas* ATCC 31554, containing rhamnose, glucose, mannose and glucuronic acid in its structure;

the biopolymer S130 generated by the strain *Alcaligenes* ATCC 31555, containing rhamnose, glucose, mannose and glucuronic acid in its molecule;

the biopolymer S139 generated by the strain *Pseudomonas* ATCC 31644, containing rhamnose, glucose, mannose, galactose and galacturonic acid in its molecule;

the biopolymer S198 generated by the strain *Alcaligenes* ATCC 31853, containing rhamnose, glucose, mannose and glucuronic acid in its molecule;

the biopolymer BM07, containing units derived from glucose, galactose and pyruvic, succinic and acetic acids in its molecule;

the biopolymer AM-2, containing glucose, rhamnose, mannose and glucuronic acid in its molecule; and the scleroglucans corresponding to the formula:

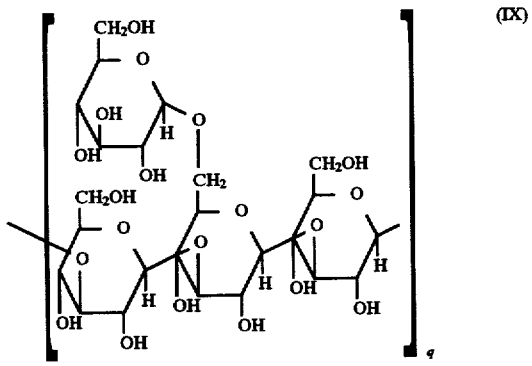

(IX)

where q varies from 500 to 1600, optionally treated with glyoxal.

5. Composition according to claim 1, where the suspending agent is combined with an inorganic derivative of silicon selected from the group consisting of the oxide and the silicates.

6. Composition according to claim 1, containing, in addition, suspending agents other than the anionic cellulose derivatives or the biopolysaccharides, chosen from:

A/The compounds of the following formula:

(X)

in which R' is an aliphatic radical with a long carbon chain, optionally interrupted by oxygen atoms, and X is a carboxylic, sulphuric or phosphoric acid residue or a radical derived from a carboxylic acid or an amide;

B/The oxides of dimethyl($C_{16}$–$C_{22}$)alkylamines;

C/The compounds of formula:

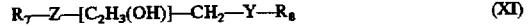

(XI)

in which:

$R_7$ and $R_8$, which are identical or different, denote $C_{12}$–$C_{20}$ linear alkyl groups;

Z denotes an oxygen atom, a sulphur atom or a sulphoxide group;

Y denotes an oxygen atom, a sulphur atom, a sulphoxide group or a methylene group;

the sum of the number of carbon atoms of $R_7$ and $R_8$ varies from 24 to 40;

when Z or Y denotes sulphoxide, Y or Z does not denote sulphur.

7. Composition according to claim 6, where the suspending agents of formula (X) are chosen from those in which:

(i) R' is a $C_{11}$–$C_{21}$ alkyl or alkenyl radical, and X is:

a group COOA where A is a mono- or polyhydroxyalkyl radical derived from a $C_2$–$C_3$ polyol or a radical $CH_2CH_2SO_3M$ where M denotes an alkali metal, ammonium or a $C_1$–$C_4$ alkanolamine residue;

a group $CO(OCH_2CH_2)_r$—OH where r has a value of between 2 and 150;

a group

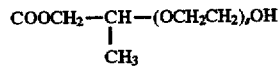

where s has a value of between 2 and 150; the free OH functional groups of the groups defined above being able to be esterified with an acid R"COOH where R" is a $C_{11}$–$C_{21}$ alkyl or alkenyl;

a group $CONR_4R_5$ where $R_4$ and $R_5$ represent hydrogen or $C_1$–$C_4$ hydroxyalkyl, one at least representing a $C_1$–$C_4$ hydroxyalkyl;

a group $OSO_3M$ or $1/3\ PO_4^{3-}M_3$ where M represents an alkali metal, ammonium or a $C_1$–$C_4$ alkanolamine residue;

(ii) R' denotes a radical $R_6(OC_2H_4)_1$—$OCH_2$ and X denotes a group COOM where M has the meaning shown above, $R_6$ denoting a $C_{12}$–$C_{14}$ alkyl radical and 1 an integer or a decimal number of between 2.5 and 10; or else $R_6$ denotes oleyl and 1 varies from 2 to 9 or else $R_6$ denotes ($C_8$–$C_9$)-alkylphenyl and 1 varies from 4 to 8;

(iii) R' denotes a ($C_{12}$–$C_{16}$)alkyl ether group and X a group $CONR_4R_5$, in which $R_4$ and $R_5$ have the same meaning as that shown above.

8. Composition according to claim 1, which has a pH of between 2 and 9.

9. Composition according to claim 1, where the aqueous medium consists of water or a mixture of water and a cosmetically acceptable solvent selected from the group consisting of the $C_1$–$C_4$ lower alcohols, the alkylene glycols and the glycol ethers.

10. Composition according to claim 1, being present in the form of a thick liquid, gel, cream or aerosol foam.

11. Process for washing and cosmetic treatment in order to remove dandruff from the hair and the scalp, comprising the steps of applying a composition as defined according to claim 1 to the hair and scalp, and then rinsing.

* * * * *